United States Patent [19]

Nakagawa et al.

[11] 4,200,632
[45] Apr. 29, 1980

[54] 2-HYDROXY BENZAMIDE DERIVATIVES AND USE THEREOF AS FUNGICIDES

[75] Inventors: Taizo Nakagawa, Ageo; Kaoru Ohmori, Okegawa; Seiji Mochizuki, Ageo; Eiichi Tanaka, Ageo; Osamu Yamada, Ageo, all of Japan

[73] Assignee: Nippon Kayaku Kabushiki Kaisha, Tokyo, Japan

[21] Appl. No.: 938,248

[22] Filed: Aug. 30, 1978

[30] Foreign Application Priority Data

Sep. 1, 1977 [JP] Japan .................. 52/104226

[51] Int. Cl.$^2$ .................. A01N 9/24; C07C 103/19
[52] U.S. Cl. .................. 424/230; 260/559 S
[58] Field of Search .................. 424/230; 260/559 S

[56] References Cited

U.S. PATENT DOCUMENTS 4,055,640  10/1977  Hirose et al. .................. 424/230

OTHER PUBLICATIONS

Chemical Abstracts 34:7882[9] (1940).
Chemical Abstracts 81:49407z (1974).
Chemical Abstracts 32:3762[9] (1938).
Chemical Abstracts 33:7760[4] (1939).
Chemical Abstracts 33:3778[7] (1939).
Chemical Abstracts 34:4731[1] (1940).
Chemical Abstracts 35:5502[9] (1941).
Chemical Abstracts 35:6250[3] (1941).
Chemical Abstracts 37:2361[9] (1943).
Chemical Abstracts 62:2734[h] (1965).
Chemical Abstracts 75:151233c (1971).
Ann. Appl. Biol. (1973), 75, 49–55.

*Primary Examiner*—Leonard Schenkman
*Attorney, Agent, or Firm*—Russell & Nields

[57] ABSTRACT

A compound represented by the formula:

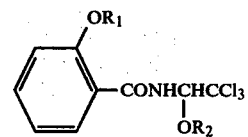

wherein $R_1$ is hydrogen or alkyl-carbonyl wherein the alkyl has 1 to 6 carbon atoms and $R_2$ is alkyl having 1 to 18 carbon atoms or phenyl and use thereof as fungicide.

20 Claims, No Drawings

2-HYDROXY BENZAMIDE DERIVATIVES AND USE THEREOF AS FUNGICIDES

BACKGROUND OF THE INVENTION

Heretofore, the prevention of soil born plant diseases was very difficult and development of a good fungicide has been especially desired. For example, the damages of Cruciferous plants attacked by clubroot have been increasing year by year.

Clubroot is a very serious disease when susceptible varieties of any cruciferous species such as cauliflower, mustard, radish, cabbage, rape and turnip are grown in infested fields, and losses caused by it are sometimes very heavy. Fields once infested with the clubroot pathogen remain so indefinitely and become unfit for cultivation of crucifers practically forever or until costly methods and materials are used to sterilize the soil.

Various preventive measures by means of fungicide against the soil born plant diseases are actually tried, however, no satisfactory result is obtained with conventional medicines and thus these are not favorable for the practical use. Thus, at present, no satisfactory soil fungicide is commercially available because one fungicide has such disadvantages that no sufficient preventive effect is obtained thereby unless a high concentration of the fungicide is disposed and this results that the fungicide is liable to remain into the plant body and/or in the soil, another has a high toxicity to men and/or beasts, another has liable to cause a phytotoxity and another has an irritative smell or unpleasant odor.

For example, an environment pollution problem is caused because mercury compounds have a high toxicity and chloropicrin has toxicity and irritative smell.

The inventors have undertaken the research for developing a soil fungicide free of defects mentioned above and found the fact that the compounds of the formula (I) have shown a high prevention effect against the soil born plant diseases, especially having a distinguished effect against clubroot of Cruciferous plants even with a low concentration.

SUMMARY OF THE INVENTION

The present invention relates to new 2-hydroxy benzamide derivatives represented by the formula:

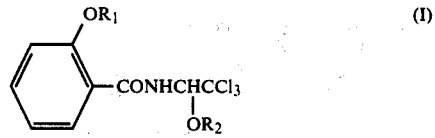

wherein $R_1$ is hydrogen or alkylcarbonyl wherein the alkyl has 1 to 6 carbon atoms and $R_2$ is alkyl having 1 to 18 carbon atoms or phenyl, a fungicidal composition comprising 0.5 to 95% by weight of said new 2-hydroxy benzamide derivatives and 99.5 to 5% by weight of adjuvants and a method for preventing or curing soil born plant diseases caused by fungi which comprises treating soil containing the fungi with an effective amount of said new 2-hydroxy benzamide derivatives.

Said compounds of the present invention have an extremely low toxicity ot men or beasts, giving no damages to the plants, without an irritative smell or unpleasant odor, presenting an effect for the control of soil born plant diseases, especially clubroot even if used in a small amount and so causing no environmental pollution problem and can be used as an ideal soil fungicide.

DETAILED DESCRIPTION OF THE INVENTION

Preferred compunds are those of the formula (I) wherein $R_1$ is hydrogen or alkylcarbonyl wherein the alkyl has 1 to 6 carbon atoms especially 1 to 3 carbon atoms and $R_2$ is alkyl having 1 to 18 carbon atoms especially 1 to 4 and 8 carbon atoms or phenyl, more preferably $R_1$ is hydrogen or acetyl and $R_2$ is alkyl having 1 to 4 carbon atoms or phenyl or $R_1$ is acetyl and $R_2$ is methyl or ethyl or phenyl.

Said compounds of the present invention are prepared by the process mentioned hereunder.

The compound of the formula:

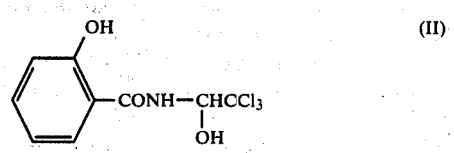

is reacted with a halogenating agent to obtain a compound of the formula:

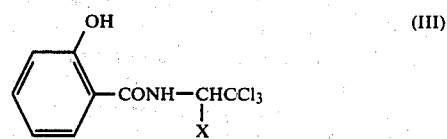

(wherein X represents halogen) and then reacted with a compound of the formula:

$$R_2OH \quad\quad\quad (IV)$$

(wherein $R_2$ is the same as mentioned above) to obtain a compound of the formula (I) wherein $R_1$ is hydrogen. These compounds also can be obtained by the direct reaction of the compound of formula (II) mentioned above with an excess quantity of a compound of the formula (IV).

The compounds of the formula (I) wherein $R_1$ is alkylcarbonyl are obtained by reacting a compound of the formula (I) wherein $R_1$ is hydrogen with an acid halide or acid anhydride of the carboxylic acid of the formula:

$$R_3COOH \quad\quad\quad (V)$$

(wherein $R_3$ is alkyl having 1 to 6 carbon atoms) in the presence of a base.

The compound of the formula (II) is disclosed in Chemical Abstract, Vol. 34, 7882-9 and is prepared by reacting salicylamide with chloral according to the process referred to Beilstein E-II, 10, 57.

As the halogenating agent for the compound of the formula (II) there can be used for example thionyl chloride or phosphor halides and thionyl chloride is specifically preferable. The reaction of the compound of the formula (II) with the halogenating agent is carried out in an innert solvent at 0° C. to 150° C. for the sufficient reaction time of 30 minutes to several hours. Said innert solvent includes such aliphatic or aromatic hydrocarbons that may be halogenated to any extent as benzene, toluene, xylene, benzine, chloromethylene, chloroform, carbon tetrachloride and chlorobenzene, ethers such as diethylether, dibutylether or dioxane, and nitriles such as acetonitrile or propionitrile, and others.

The reaction of a compound of the formula (III) with a compound of the formula (IV) is carried out in said innert solvent, if required in the presence of a base, at 0° C. to 150° C. for several hours. The compounds of the formula (IV) include branched or non-branched aliphatic alcohols (for example, methyl alcohol, ethyl alcohol, propyl alcohol, butyl alcohol, pentyl alcohol, hexyl alcohol, octyl alcohol, dodecyl alcohol, octadecyl alcohol) or phenol. And as the base are used alkali metal carbonates and alkali metal alcoholates (for example, sodium carbonate, sodium methylate, sodium ethylate and potassium carbonate, potassium methylate, potassium ethylate) and aliphatic, aromatic or heterocyclic amines (for example, triethylamine, dimethylaniline, dimethylbenzylamine and pyridine).

In the case of directly reacting an excess quantity of a compound of the formula (IV) with the compound of the formula (II) for several to twenty hours at 60° to 150° C. a compound of the formula (I) wherein $R_1$ is hydrogen is obtained. And, at this time, it is preferably to add a suitable catalyst such as hydrogen chloride or sulfuric acid in order to accelerate the reaction. As the acid halide of the carboxylic acid of the formula (V), for example, acetyl chloride or propionyl chloride can be used. The reaction of a compound of the formula (I) wherein $R_1$ is hydrogen with said acid chloride is carried out in an innert solvent in the presence of a base at the temperature of 0° to 100° C. for 30 minutes to several hours to obtain a compound of the formula (I) wherein $R_1$ is the alkylcarbonyl. As the innert solvent other than the examples mentioned above there can be used ketones (for example, acetone, methylethylketone, methylisopropylketone), esters (for example, methyl acetate, ethyl acetate) and pyridine.

And, the reaction of an acid anhydride of the carboxylic acid of the formula (V) and a compound of the formula (I) wherein R is hydrogen is carried out preferably in the presence of a catalyst, for example, triethylamine, pyridine, or sulfuric acid, at 60° to 120° C. and is completed in several hours.

The typical compounds of the present invention prepared by the procedures mentioned above are shown in Table-1.

TABLE 1

| Compound No. | Formula | Physical property: melting point or refractive index |
|---|---|---|
| 1 | 2-OH, CONHCHCCl₃, OCH₃ (on α-carbon) | m.p. 115°–117° C. |
| 2 | 2-OH, CONHCHCCl₃, OC₂H₅ | m.p. 123°–124° C. |
| 3 | 2-OH, CONHCHCCl₃, OC₃H₇ (n) | m.p. 121°–121.5° C. |
| 4 | 2-OH, CONHCHCCl₃, OC₃H₇ (i) | m.p. 121°–121.5° C. |
| 5 | 2-OH, CONHCHCCl₃, OC₄H₉ (n) | m.p. 73°–74° C. |
| 6 | 2-OH, CONHCHCCl₃, OC₈H₁₇ | $n_D^{25}$ 1.5270 |
| 7 | 2-OH, CONHCHCCl₃, O-phenyl | m.p. 143°–145° C. |
| 8 | 2-OCOCH₃, CONHCHCCl₃, OCH₃ | m.p. 145°–146° C. |
| 9 | 2-OCOCH₃, CONHCHCCl₃, OC₂H₅ | m.p. 93.5°–94° C. |
| 10 | 2-OCOCH₃, CONHCHCCl₃, OC₃H₇ (n) | m.p. 76°–77° C. |
| 11 | 2-OCOCH₃, CONHCHCCl₃, OC₈H₁₇ | $n_D^{25}$ 1.5085 |
| 12 | 2-OCOCH₃, CONHCHCCl₃, O-phenyl | m.p. 156°–157° C. |
| 13 | 2-OCOC₂H₅, CONHCHCCl₃, OC₂H₅ | m.p. 56°–57° C. |
| 14 | 2-OCOC₂H₅, CONHCHCCl₃, O-phenyl | m.p. 133°–134° C. |

For further illustration of the preparative methods of the compounds in the present invention, the following examples are given.

EXAMPLE 1

N-(1'-methoxy-2',2',2'-trichloroethyl)-2-hydroxy benazmide (Compound No. 1)

2,500 ml of benzene was added to 1,423 g of N-(1'-hydroxy-2',2',2'-trichloroethyl)-2-hydroxy benzamide and then 833 g of thionyl chloride was added thereto and heated under reflux at 70°–80° C. for 4 hours to obtain N-(1',2',2',2'-tetrachloroethyl)-2-hydroxy benzamide (white crystal, melting point of 113°–113.5° C., Anal. Found: C,35.74; H,2.12; N,4.70 Calcd. for $C_9H_7Cl_4NO_2$: C,35.68; H,2.33; N,4.62 and the resultant reaction mixture, without separation of the crystals, was cooled to below 30° C. and mixed with 1,250 g of methanol and heated under reflux for 2 hours at 55°–60° C. followed by removing the solvent and the residue was poured into water, filtered and dried to obtain 1,380 g (yield 92.4%) white crystals of N-(1'-methoxy-2',2',2'-trichloroethyl)-2-hydroxy benzamide.

Melting point: 117°–118° C.

| Elementary analysis: | C | H | N |
|---|---|---|---|
| Calcd. | 40.23% | 3.38% | 4.69% |
| Found | 40.41 | 3.38 | 4.73 |

The compounds No. 2 to No. 7 were prepared by similar procedures.

EXAMPLE 2

N-(1'-methoxy-2',2',2'-trichloroethyl)-2-acetoxy benzamide (Compound No. 8)

To 2.5 g of N-(1'-methoxy-2',2',2'-trichloroethyl)-2-hydroxy benzamide was added 20 g of pyridine and maintained at below −10° C., 1.5 g of acetyl chloride was added dropwise and then allowed at room temperature for about 30 minutes, and poured into water to give a crystal which was recrystalized by using methanol to obtain 2.2 g white crystal of N-(1'-methoxy-2',2',2'-trichloroethyl)-2-acetoxy benzamide.

Melting point: 145°–146° C.

| Elementary analysis: | C | H | N |
|---|---|---|---|
| Calcd. | 42.32% | 3.55% | 4.11% |
| Found | 42.66 | 3.52 | 4.31 |

Similar procedures gave the compounds No. 9 to No. 14.

The compounds of the present invention are used as a soil fungicide sometimes solely but usually in a various type of formulations, with carriers or other adjuvants, such as emulsion, wettable powder dusts, granules, micro granules in compliance with the requirement of the purposes. In this case, the content of a compound of the formula (I) in the formulations is satisfactory with the same as of the effective component in conventional formulations of 0.5 to 95% (hereinafter % represents by weight basis unless otherwise noted), preferably 2 to 70%. The content of adjuvants in the formulations is, therefore, 99.5%, to 5%, preferably 98 to 30%.

Both solid carriers and liquid carriers can be used and the solid carriers include clay, kaolin, talc, diatomaceous earth, silica, calcium carbonate, and the liquid carriers include benzene, alcohols, acetone, xylene, methylnaphthalene, cyclohexanes, dimethylformamide, dimethylsulfoxide, animal or vegetable oils, aliphatic acids, aliphatic esters, and surface active agents. And such adjuvants other than carriers usually used in agricultural chemicals as spreading agents, emulsifiers, wetting agents, dispersing agents, fixing agents can be properly mixed in order to assure the effects. The compounds of the formula (I) can be used in blending with other herbicides, insecticides, acaricides, agricultural and horicultural fungicides, soil fungicide, soil stabilizers, or fertilizers.

Further detailed formulation examples of the present invention are explained hereunder, however, the kinds of the additives and the mixing ratios should not be limited within the range of the examples but can be utilized in wider ranges for practical uses.

Wherein, "part (s)" means part(s) by weight.

FORMULATION EXAMPLE 1: Dusts 10 parts of the compound No. 1 of the present invention (N-(1'-methoxy-2',2',2'-trichloroethyl)-2-hydroxy benzamide) and 41 parts of talc and 49 parts of clay were mixed and pulverized to obtain a dust.

FORMULATION EXAMPLE 2: Wettable powder 80 parts of the compound No. 8 (N-(1'-methoxy-2',2',2'-trichloroethyl)-2-acetoxy benzamide) of the present invention, 15 parts of kaolin, 3 parts of a sodium higher alkyl sulfate and 2 parts of a sodium polyacrylate are mixed and pulverized to obtain a wettable powder.

FORMULATION EXAMPLE 3: Granules 3 parts of the compound No. 3 (N-(1'-n-propyloxy-2',2',2'-trichloroethyl)-2-hydroxy benzamide) of the present invention, 35 parts of diatomaceous earth, 23 parts of bentonite, 37 parts of talc and 2 parts of a breaking agent were mixed and 18 parts of water were added to moisten the mixture homogeneously and then extruded through a injection molder to make granules which were dried and submitted to a crusher, regranulated by means of a granulator to obtain granules having a particle size of 0.6 to 1 mm.

FORMULATION EXAMPLE 4: Micro granules 5 parts of the compound No. 13 (N-(1'-ethoxy-2',2',2'-trichloroethyl)-2-propionyl benzamide) of the present invention were homogeneously mixed with 6 parts of bentonite and 9 parts of clay to make a concentrated powder mixture. Separately 80 parts of non-absorbent coarse mineral powder of 105 to 74 microns size were placed in a proper mixing machine into which 20 parts of water is added in rotating to moisten followed by adding the above mentioned concentrated powder mixture to coat, dried to obtain micro granules.

FORMULATION EXAMPLE 5: Emulsion 20 parts of the compound No. 7 (N-(1'-phenyloxy-2',2',2'-trichloroethyl)-2-hydroxy benzamide) were dissolved in 63 parts of xylene, into which 17 parts of the mixture of alkylphenol-ethylene oxide condensate and a calcium alkylbenzene sulfonate (8:2) is mixed and dissolved to obtain emulsion. This emulsion is used after diluting with water.

Although the compounds of the present invention can be used for soil treatment even per se, they are usually formulated as mentioned above and used for the soil treatment. The quantity of the compounds of the present invention useable for the purpose of soil treatment is varied depending on the kind of the compounds, using method, and formulations, and is difficult to be generally determined but usually 1 to 8 kg/10 a, preferably 2 to 8 kg/10 a, in the case of overall soil treatment, for the case of furrow treatment 0.5 to 6 kg/10 a and preferably 1 to 5 kg/10 a, and for treating the planting holes 0.1 to 2 g/plant and preferably 0.3 to 0.7 g/plant.

The advantageous effects of the present invention are shown by the following experimental results.

TEST EXAMPLE 1

Exterminating test on chinese cabbage clubroot

A pot of 15 cm diameter was filled with soil infected by the pathogenic fungi of said disease (*Plasmodiophora brassicae*) and mixed well with a 10% dust of the composition of the present invention prepared by the same procedure as of the Formulation Example 1 in an amount of 2 g in each pot. Thereafter the seeds of chinese cabbage (variety: Taibyo 60-nichi) were sowed at 15 seeds per pot. The pot was buried in the field to make the plant attacked by the pathogen.

A dust containing 20% of PCNB (active component: pentachloro-nitrobenzene) was used as a control and tested in the same procedure as mentioned above.

4 weeks after sowing, the chinese cabbages were taken up and attack by the pathogen was observed and a "Percentage of healthy seedlings" was calculated as follows.

Percentage of healthy seedlings $$\frac{\text{number of healthy plants in each pot}}{\text{number of observed plants in each pot}} \times 100$$

The results are shown in Table-2.

TABLE 2

| | Compound NO. | Active component quantity (per pot) | Percentage of healthy seedlings | Phyto-toxicity |
|---|---|---|---|---|
| Present invention | 1 | 0.2g | 93% | none |
| | 2 | " | 90 | " |
| | 3 | " | 85 | " |
| | 4 | " | 87 | " |
| | 5 | " | 83 | " |
| | 7 | " | 98 | " |
| | 8 | " | 90 | " |
| | 12 | " | 95 | " |
| | 14 | " | 93 | " |
| Control | dust containing 20% PCNB | 0.4g | 78 | " |
| | Blank | — | 7 | — |

TEST EXAMPLE 2

Exterminating test on cabbage clubroot

In the test field infected by the pathogenic fungi of said disease (*Plasmodiophora brassicae*), micro granules containing 5% of a compound of the present invention was applied into the furrows at the rate of 40 kg per 10 a followed by planting the cabbages (variety: Kinsyu) of 5 leaves stage. The area of one plot was 4.8 m².

A dust containing 20% PCNB (active component: pentachloronitrobenzene) was used as a control and tested in the same procedure as mentioned above.

2 months after the planting, the cabbages were taken up and degree of attack by pathogen was observed and percentage of diseased plant and diseased index was calculated.

Diseased index =
$$\frac{(8 \times A) + (6 \times B) + (4 \times C) + (2 \times D) + (1 \times E)}{8 \times (A + B + C + D + E + F)} \times 100$$

Wherein
A: The number of plants in which the growing of clubroot is remarkable at the main roots and side roots, commencing decomposition thereof.
B: The number of plants of which a part of the main root is swollen by the infection of clubroot and the side roots are remarkably swollen.
C: The number of plants of which the side roots are remarkably swollen by the infection of clubroot.
D: The number of plants of which the side roots are swollen by the infection of clubroot gall.
E: The number of plants of which the side roots are slightly swollen by the infection clubroot.
F: The number of healthy plants.

The test results are shown in Table-3.

TABLE 3

| Compound | Active component quantity (per 10a) | Percentage of diseased plant | Diseased index | Phyto-toxicity |
|---|---|---|---|---|
| The present invention: | | | | |
| Compound No.1 | 2 kg | 65.4% | 36.7 | none |
| No.7 | 2 kg | 30.5 | 21.3 | none |
| Control: dust contain 20% PCNB | 5 kg | 87.5 | 61.9 | none |
| Blank | — | 100.0 | 87.6 | |

TEST EXAMPLE 3

Exterminating test against chinese cabbage clubroot (Test for the remaining effects)

A pot of 15 cm diameter was filled with soil infected by the pathogenic fungi of said disease (*Plasmodiophora brassicae*) into which a dust containing 10% of the compound of the present invention prepared by the same procedure as of the Formulation Example 1 was added at the rate of 1 or 2 g per 1 liter of the infected soil, after well mixing followed by being buried into the soil in a greenhouse, and 40 days after such treatment by the compound, sowing the seeds of chinese cabbage (variety: Taibyo 60-nichi) at 20 seeds per pot.

A dust containing 20% of PCNB was used as a control and tested in the same procedure as mentioned above.

31 days after the seeding the chinese cabbage were taken up and observed to calculate the percentage of diseased seedlings and diseased index. The diseased index is given by the following equation.

diseased index =
$$\frac{(A \times 4) + (B \times 3) + (C \times 2) + (D \times 1)}{4 \times (A + B + C + D + E)} \times 100$$

wherein
A: The number of the plants of which remarkable growing of clubroot gall is observed.
B: The number of plants in which clubroot gall is formed at the upper part of the mainroots.

C: The number of the plant in which clubroot gall is formed at the lower part of the main roots.
D: The number of the plants in which clubroot gall is formed at the side roots.
E: The number of healthy plants.

The test results are shown in Table-4.

TABLE 4

| Compound | Active component quantity (per 1 liter of infected soil) | Percentage of diseased seedlings | Diseased index | Phytotoxicity |
|---|---|---|---|---|
| Compound No.7 of the present invention | 0.1g | 3 | 3 | none |
|  | 0.2g | 0 | 0 | none |
| Dust containing 20% PCNB | 0.2g | 25 | 21 | none |
|  | 0.4g | 7 | 4 | none |
| Blank | — | 55 | 38 | — |

TEST EXAMPLE 4

Exterminating test against small turnip clubroot

A pot of 15 cm diameter was filled with the soil infected by the pathogenic fungi of said disease (*Plasmodiophora brassicae*) into which a dust containing 10% of the compound of the present invention prepared by the same procedure as of the Formulation Example 1 was added at the rate of 1 or 2 g per pot and well mixed, followed by sowing the seeds of small turnip at 20 seeds per pot, and buried into the soil in a greenhouse.

A dust containing 20% of PCNB was used as a control and tested in the same procedure as mentioned above.

On the 49th day from the seeding, the small turnips were taken up and observed to obtain the number of diseased seedlings and the diseased index. The test results are shown in Table-5.

TABLE 5

| Compound | Active component quantity (per 1 liter of infected soil) | Percentage of diseased seedlings (%) | Diseased index | Phytotoxicity |
|---|---|---|---|---|
| Compound No.7 of the present invention | 0.1g | 8 | 4 | none |
|  | 0.2g | 2 | 1 | none |
| Dust contaning 20% PCNB | 0.2g | 89 | 70 | none |
|  | 0.4g | 79 | 55 | none |
| Blank | — | 89 | 70 | — |

TEST EXAMPLE 5

Exterminating test on damping-off of cucumber seedling

A pot of 12 cm diameter was filled with field soil infected by adding 3 g of the soil which was inoculated with *Rhizoctonia solani*, bran media at each 3 g uniformly covering the soil surface.

After the application of the pathogenic fungi, cucumber seeds (variety: Ohyashima) were sowed at 10 seeds per pot followed by drenching a diluted suspension of 80% wettable powder containing the compound of the present invention prepared by the same procedure as of the Formulation Example 2 at 50 milli-liters per pot. The attacking by the disease was made in a greenhouse.

A wettable powder containing 50% of PCNB (active component: pentachloro-nitrobenzene) was used as a control and tested in the same procedure as mentioned above.

10 days after the seeding, the cucumber seedlings was digged up and the healthy seedlings was calculated.

$$\text{Healthy seedlings} = \frac{\text{The number of healthy seedlings in each treated pot}}{\text{The number of germination in untreated and non-fungi-applied pot}} \times 100$$

The test results are shown in Table-6.

TABLE 6

| Compound | Concentration of active component (ppm) | Percentage of healthy seedling | Phythotoxicity |
|---|---|---|---|
| (Present invention) |  |  |  |
| 1 | 1,000 | 100(%) | none |
| 2 | " | 100 | " |
| 3 | " | 100 | " |
| 4 | " | 100 | " |
| 5 | " | 95 | " |
| 6 | " | 85 | " |
| 8 | " | 100 | " |
| 9 | " | 100 | " |
| 10 | " | 95 | " |
| 11 | " | 85 | " |
| 13 | " | 85 | " |
| (Control) PCNB 50% wettable powder | 1,000 | 95 | none |
| With fungi, un-treated section | — | 0 | — |
| Without fungi, un-treated section | — | 100 | — |

TEST EXAMPLE 7

Test for damages of Cruciferae plants by fungicide

In the field, a dust containing 10% of the compound of the present invention prepared by the same procedure as of the Formulation Example 1 was applied at respective 40 kg, 60 kg, 80 kg and 100 kg per 10 a, followed by sowing the seeds of small turnip (variety: Someya-kanamachi), chinese cabage (variety: Taibyo 60-nichi) and Rutabaga (variety: mazestic-No1). 34 days after the seeding, the phytotoxity was examined by exterior visual observation as to the plant size and others. The test results are shown in Table-7.

TABLE 7

| Compound No. | Active component quantity | Phytotoxicity |  |  |
|---|---|---|---|---|
|  |  | small turnip | chinese cabbage | Rutabaga |
| No. 7 | 4kg/10a | none | none | none |
|  | 6kg/10a | " | " | " |
|  | 8kg/10a | " | " | " |
|  | 10kg/10a | " | " | " |

What we claim is:
1. A compound represented by the formula:

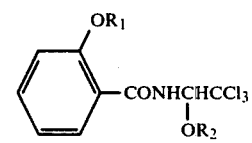

wherein $R_1$ is hydrogen or alkyl-carbonyl wherein the alkyl has 1 to 6 carbon atoms and $R_2$ is alkyl having 1 to 18 carbon atoms or phenyl.

2. The compound according to claim 1 wherein $R_1$ is hydrogen or alkyl carbonyl wherein the alkyl has 1 to 3 carbon atoms and $R_2$ is alkyl having 1 to 4 or 8 carbon atoms or phenyl.

3. The compound according to claim 2 wherein $R_1$ is hydrogen or acetyl $R_2$ is alkyl having 1 to 4 carbon atoms or phenyl.

4. The compound according to claim 3 wherein $R_1$ is hydrogen and $R_2$ is phenyl.

5. The compound according to claim 3 wherein $R_1$ is hydrogen and $R_2$ is methyl.

6. A fungicidal composition for agriculture comprising 0.5 to 95% by weight of a compound of the formula:

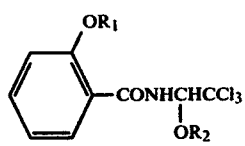

wherein $R_1$ is hydrogen or alkylcarbonyl wherein the alkyl has 1 to 6 carbon atoms, $R_2$ is alkyl having 1 to 18 carbon atoms or phenyl and 99.5 to 5% (by weight) of adjuvants.

7. The fungicidal composition according to claim 6 wherein R is hydrogen or alkyl carbonyl wherein the alkyl has 1 to 3 carbon atoms and $R_2$ is alkyl having 1 to 4 or 8 carbon atoms or phenyl.

8. The fungicidal composition according to claim 6 wherein $R_1$ is hydrogen or acetyl and $R_2$ is alkyl having 1 to 4 carbon atoms or phenyl.

9. The fungicidal composition according to claim 8 wherein $R_1$ is hydrogen and $R_2$ is phenyl.

10. The fungicidal composition according to claim 8 wherein $R_1$ is hydrogen and $R_2$ is methyl.

11. A method for preventing soil born plant diseases caused by fungi which comprises treating soil containing the fungi with an effective amount of a compound represented by the formula:

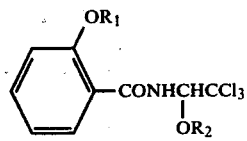

wherein $R_1$ is hydrogen or alkylcarbonyl wherein the alkyl has 1 to 6 carbon atoms and $R_2$ is alkyl having 1 to 18 carbon atoms or phenyl.

12. The method according to claim 11 wherein $R_1$ is hydrogen or alkyl-carbonyl wherein the alkyl has 1 to 3 carbon atoms and $R_2$ is alkyl having 1 to 4 or 8 carbon atoms or phenyl.

13. The method according to claim 12 wherein $R_1$ is hydrogen or acetyl, $R_2$ is alkyl having 1 to 4 carbon atoms or phenyl.

14. The method according to claim 13 wherein $R_1$ is hydrogen and $R_2$ is phenyl.

15. The method according to claim 13 wherein $R_1$ is hydrogen and $R_2$ is methyl.

16. A method for the control of clubroot caused by *Plasmodiophora brassicae* which comprises applying to said fungi an effective amount of a compound as claimed in claim 1.

17. The method according to claim 16 wherein $R_1$ is hydrogen or alkylcarbonyl where the alkyl has 1 to 3 carbon atoms and $R_2$ is alkyl having 1 to 4 or 8 carbon atoms or phenyl.

18. The method according to claim 17 wherein $R_1$ is hydrogen or acetyl and $R_2$ is alkyl having 1 to 4 carbon atoms or phenyl.

19. The method according to claim 18 wherein $R_1$ is hydrogen and $R_2$ is phenyl.

20. The method according to claim 18 wherein $R_1$ is hydrogen and $R_2$ is methyl.

* * * * *